(12) United States Patent
Wruck et al.

(10) Patent No.: US 11,730,911 B2
(45) Date of Patent: Aug. 22, 2023

(54) CONTROL SYSTEM AND PROCESS FOR CONTROLLING THE DISPENSING OF FRESH GAS FOR AN ANESTHESIA DEVICE

(71) Applicant: Drägerwerk AG & Co. KGaA, Lübeck (DE)

(72) Inventors: Norbert Wruck, Lübeck (DE); Robert Schmid, Lübeck (DE); Ulf Pilz, Lübeck (DE); Daniel Wolansky, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 688 days.

(21) Appl. No.: 16/832,028

(22) Filed: Mar. 27, 2020

(65) Prior Publication Data

US 2020/0306487 A1    Oct. 1, 2020

(30) Foreign Application Priority Data

Mar. 29, 2019  (DE) ...................... 10 2019 002 273.4

(51) Int. Cl.
*A61M 16/10* (2006.01)
*A61M 16/18* (2006.01)
*A61M 16/01* (2006.01)

(52) U.S. Cl.
CPC .......... *A61M 16/104* (2013.01); *A61M 16/01* (2013.01); *A61M 16/18* (2013.01);
(Continued)

(58) Field of Classification Search
CPC .. A61M 16/01; A61M 16/104; A61M 16/026; A61M 16/18; A61M 2016/026;
(Continued)

(56) References Cited

U.S. PATENT DOCUMENTS 5,497,767 A * 3/1996 Olsson .................. A61M 16/00
                                                        128/205.13
5,806,513 A * 9/1998 Tham ................. A61M 16/1015
                                                        128/203.14
(Continued)

FOREIGN PATENT DOCUMENTS

CN        104288884 A     1/2015
EP          2572748 A1    3/2013
(Continued)

*Primary Examiner* — Colin W Stuart
*Assistant Examiner* — Douglas Y Sul
(74) *Attorney, Agent, or Firm* — McGlew and Tuttle, P.C.

(57) ABSTRACT

A control system controls fresh gas dispensing for an anesthesia device, with a patient gas-measuring unit, an anesthetic-dispensing unit, a user interface, and a fresh gas regulation unit. With a transition from deactivated assistance mode to activated assistance mode, a processing unit receives a measured signal, a fresh gas signal and an assistance signal and calculates an end tidal anesthetic concentration over time based on a current volume flow, a predefined volume flow and on a current end tidal anesthetic concentration and stores this as a preset curve. A fresh gas correction signal is output upon the determined current end tidal anesthetic concentration leaving a surrounding range of the preset curve. A predefined volume flow curve is changed as a function of the correction signal. The volume flow of fed fresh gas is increased when the surrounding range is undershot and is reduced when the surrounding range is exceeded.

20 Claims, 5 Drawing Sheets

(52) U.S. Cl.
    CPC ............... *A61M 2205/3379* (2013.01); *A61M 2205/502* (2013.01)

(58) Field of Classification Search
    CPC .... A61M 2016/1035; A61M 2205/502; A61M 2205/3334; A61M 2205/583; A61M 2205/3379
    See application file for complete search history.

(56) References Cited

U.S. PATENT DOCUMENTS

| | | | |
|---|---|---|---|
| 2002/0014236 A1* | 2/2002 | Dittmann | A61M 16/01 128/204.23 |
| 2009/0050148 A1* | 2/2009 | Heinonen | A61M 16/104 128/203.14 |
| 2009/0199854 A1* | 8/2009 | Heinonen | A61M 16/18 128/203.14 |
| 2010/0101571 A1* | 4/2010 | Messerges | A61M 16/104 128/203.14 |
| 2011/0094509 A1 | 4/2011 | Heinonen et al. | |
| 2011/0168177 A1* | 7/2011 | Connor | A61M 16/01 128/203.14 |
| 2012/0145152 A1 | 6/2012 | Lain et al. | |
| 2014/0352693 A1* | 12/2014 | Pessala | A61M 16/122 128/203.14 |
| 2021/0370010 A1* | 12/2021 | Tamiya | A61M 16/202 |

FOREIGN PATENT DOCUMENTS

| | | |
|---|---|---|
| EP | 2808049 A1 | 12/2014 |
| WO | 2004000400 A2 | 12/2003 |
| WO | 2007012197 A1 | 2/2007 |

* cited by examiner

CONTROL SYSTEM AND PROCESS FOR CONTROLLING THE DISPENSING OF FRESH GAS FOR AN ANESTHESIA DEVICE

CROSS REFERENCE TO RELATED APPLICATIONS

This application claims the benefit of priority under 35 U.S.C. § 119 of German Application 10 2019 002 273.4, filed Mar. 29, 2019, the entire contents of which are incorporated herein by reference.

TECHNICAL FIELD

The present invention pertains to a control system for controlling the dispensing of fresh gas for an anesthesia device, as well as to a corresponding anesthesia device. The present invention further pertains to a process for controlling the dispensing of fresh gas for an anesthesia device.

TECHNICAL BACKGROUND

Dispensing of anesthetics within a breathing gas circuit of an anesthesia device is typically carried out via the control of a volume flow of a fresh gas being fed to the breathing gas circuit and via the dispensing of a concentration of the anesthetic within this fresh gas.

In this case, it is common practice for the volume flow of the fresh gas to be reduced when the end tidal anesthetic concentration comes close to a desired anesthetic target concentration.

For such a control, it is known according to EP 2 808 049 A1 that a corresponding fully automated control of the dispensing of fresh gas and of the anesthetic concentration is carried out after a respective user input concerning the end tidal target concentration of the anesthetic and a desired control profile of the fresh gas feed for reaching the end tidal target concentration.

It is further known for such fully automated controls to graphically output a likely future curve of the end tidal anesthetic concentration for a user of the anesthesia device according to current measured values.

SUMMARY

An object of the present invention is to provide an improved control of the dispensing of fresh gas of an anesthesia device, and in particular a control with a reliably predictable, future curve of the anesthetic concentration.

A control system for controlling the dispensing of fresh gas for an anesthesia device, with at least one patient gas-measuring unit, with an anesthetic-dispensing unit, with a user interface, with a fresh gas regulation unit and with a processing unit is proposed according to a first aspect of the present invention to accomplish this object.

The at least one patient gas-measuring unit is arranged in a breathing gas circuit of the anesthesia device and is configured to determine an end tidal anesthetic concentration in the breathing gas circuit and to output a corresponding measured signal at regular time intervals. The anesthetic concentration in the breathing gas circuit is preferably determined continuously, i.e., almost without interruption over a certain period of time.

The anesthetic-dispensing unit is configured to make possible the dispensing of an anesthetic in a fresh gas being fed to the breathing gas circuit.

The user interface is configured to activate or deactivate an assistance mode of the control system when a corresponding user input is present and to output a corresponding assistance signal.

The fresh gas regulation unit is arranged and configured to receive the assistance signal and, when the assistance mode is activated, to regulate the reduction of a volume flow of the continuously fed fresh gas over time corresponding to a predefined volume flow curve. It is further configured to output at regular time intervals a fresh gas signal, which indicates the current volume flow of the continuously fed fresh gas.

The processing unit is configured to receive the measured signal and the fresh gas signal and to determine therefrom the current volume flow of the fresh gas being fed and the current end tidal anesthetic concentration in the breathing gas circuit. The processing unit is further configured to receive the assistance signal and, when a transition from deactivated assistance mode to activated assistance mode is present based on the current volume flow, on the predefined volume flow curve and on the current end tidal anesthetic concentration, to calculate an expected future curve of the end tidal anesthetic concentration over time, to output the expected future curve as preset curve and to store the preset curve. In this connection, the processing unit is further configured to output a fresh gas correction signal to the fresh gas regulation unit as soon as the defined current end tidal anesthetic concentration in the breathing gas circuit leaves an ambient range of the preset curve, which ambient range is formed around the preset curve. In this connection, the fresh gas regulation unit is further configured to receive the fresh gas correction signal and to change the predefined volume flow curve as a function of the fresh gas correction signal, wherein the volume flow of the continuously fed fresh gas is increased when the surrounding range is undershot and is reduced when the surrounding range is reduced compared to the originally predefined volume flow curve.

The present invention is based on the discovery that it is important in routine clinical practice that a given future curve of the end tidal anesthetic concentration is reliable for a user of the anesthesia device. Furthermore, it was discovered within the framework of the present invention that an automated correction of the volume flow of the fresh gas being fed may help in this case to adhere to a given future curve of the end tidal anesthetic concentration. This is achieved according to the present invention by a surrounding range around the calculated preset curve being assumed and in case current measured values leave this surrounding range, the fresh gas correction signal is outputted for the correction of the quantity of fresh gas being provided.

The control system according to the present invention advantageously makes it possible to reliably predict how the future curve of the end tidal anesthetic concentration will be since any deviation from this curve is corrected. As a result, the work of an anesthetist is simplified and predictability is established for the development of the end tidal anesthetic concentration during an anesthesia.

Furthermore, the control system according to the present invention advantageously makes possible an automated control, which is possible without an automated operation of the anesthetic-dispensing unit. This is advantageous for the use of the anesthesia device by a direct control of the anesthetic concentration being provided being possible, without relying on an automated control in this case. Since an anesthetic concentration that is excessively high may lead to damage to the health of a person to be treated, the safety of this person is consequently increased. Furthermore, the approval process of the control system according to the present invention can advantageously be simplified for use in hospitals as a result.

The assistance mode can be activated explicitly by a corresponding manual input or implicitly by the selection of a certain functionality, which also triggers the presence of the assistance mode.

The presence of predefined time intervals is defined as regular time intervals within the framework of the present invention.

The preset curve is calculated according to the present invention only in case the assistance signal indicates a transition into the activated assistance mode. After deactivation of the assistance mode, a new future curve is calculated in case of a new activation, so that the preset curve always refers to the currently activated assistance mode.

The predefined volume flow curve is changed when leaving the surrounding range such that an oscillation characteristic of the measured anesthetic concentration is avoided. This can be achieved, for example, by changes taking place according to empirical experiences while avoiding very large jumps within the volume flow curve.

The changed predefined volume flow curve replaces the predefined volume flow curve according to the present invention and will be considered again to be the predefined volume flow curve for a subsequent correction in the sense of the present invention.

The individual devices within the control system may each be located spaced apart from each other or in a common device, for example, controlled by a common processor. The control system according to the present invention may be an integral component of an anesthesia device or may be at least partly connected to a prior-art anesthesia device in relation to the control of individual components.

Preferred embodiments of the control system according to the present invention will be described below:

In one embodiment, the control system according to the present invention has, moreover, an output unit, which is signal technology connected (signal connected) to the processing unit. The output unit is preferably configured in this case to output the preset curve with the calculated future curve of the end tidal anesthetic concentration over time. Such an output is advantageously carried out as a graphic view, for example, via a display of the output unit in a variant of this embodiment. This embodiment is especially advantageous in that the curve over time of the end tidal anesthetic concentration can thus be directly outputted to a user of the control system. To be able to detect the expected curve over time especially rapidly in the clinical setting, a graphic output is especially advantageous. The preset curve is outputted via an interface of the processing unit and displayed by an external device in an alternative or additional embodiment thereto.

In an especially preferred embodiment of the control system according to the present invention, the anesthetic-dispensing unit is configured to make it possible to dispense the anesthetic in an exclusively manually controlled manner. It can consequently be ensured that defective components within the automated control process cannot lead to an excessively high concentration of provided anesthetic. The risk of damage to the health of a person to be treated can thus be reduced. Furthermore, the control system according to the present invention is simplified by the manual control of the anesthetic-dispensing unit, since the anesthetic-dispensing unit does not have to communicate with other components of the control system. In addition, this preferred embodiment makes it possible to use an anesthetic-dispensing unit that is known and already established on the market for the control system according to the present invention.

In another especially preferred embodiment, the predefined volume flow curve comprises a continuous, degressive reduction of the volume flow over time. Such a degressive reduction of the volume flow advantageously reduces the quantity of fresh gas to be used, since a continuous increase of the end tidal anesthetic concentration without an inadvertent exceeding of a predefined anesthetic concentration can be achieved in an especially simple manner.

According to the present invention, the predefined volume flow curve of this embodiment is enhanced by a sharp increase or a sharp reduction of the volume flow due to each fresh gas correction signal. A fresh gas correction signal consequently always generates a new determination of an adapted predefined volume flow curve.

In an advantageous embodiment of the control system, the user interface is further configured to receive a fresh gas input and to output a corresponding fresh gas regulation signal, wherein the fresh gas input comprises information about a minimal volume flow of the fresh gas to be fed to the breathing gas circuit, which minimal volume flow is to be provided by means of the fresh gas regulation unit. This embodiment advantageously makes it possible to avoid volume flows which are low such that a desired end tidal anesthetic concentration cannot be maintained continuously. In particular, a user of the anesthesia device within the framework of this embodiment can regulate the volume flow curve corresponding to the user's own experiences such that the user has, furthermore, trust in the operability of the control system and does not have to fear premature waking up of the patient after anesthesia has been carried out. The volume flow of fresh gas used, for example, for sevoflurane, is typically in a range between 300 mL/min and 8 L/min. The individually set, minimal volume flow will therefore be in a range between 300 mL/min and 1 L/min. The control system is preferably configured to not allow an input of a minimal volume flow of less than 250 mL/min. 250 mL/min is the physiological minimum of fresh gas to be provided.

In a preferred variant of the above embodiment, the fresh gas regulation unit is further configured to receive the fresh gas regulation signal and to select the predefined volume flow curve from a number of predefined volume flow curves based on the fresh gas regulation signal. In this variant, the predefined volume flow curve is advantageously adapted to the requirements of a user of the control system. Furthermore, the selection of the predefined volume flow curve advantageously makes it possible to predefine an especially suitable volume flow curve for each conceivable fresh gas input at the user interface. The different predefined volume flow curves are preferably stored in a storage modulus of the fresh gas regulation unit. In an alternative variant of this embodiment, the processing unit is further configured to receive the fresh gas regulation signal, to select the predefined volume flow curve from a number of predefined volume flow curves based on the fresh gas regulation signal and to output it to the fresh gas regulation unit.

In another advantageous embodiment of the control system according to the present invention, the user interface is further configured to receive a limit concentration input and to output a corresponding limit concentration signal to the processing unit, wherein the limit concentration input comprises information about a maximum end tidal anesthetic concentration to be provided to a patient to be treated by the anesthesia device. In this embodiment, provisions are advantageously made for the anesthetic concentration in the exhaled air of the person to be treated not to exceed a predefined limit value. This can be achieved, for example, via a corresponding control, via a corresponding warning signal, or via a separate transmission of information pertaining to such an exceeding of the limit value. Consequently, it is especially possible to avoid that the person to be treated suffers damage to his health because of an excessively high dosage of the anesthetic. The desired concentration of the anesthetic, for example, for sevoflurane is typically in a range between 3 vol. % and 8 vol. %. The maximum end tidal anesthetic concentration to be provided will therefore be approximately in a range between 8 vol. % and 12 vol. % as a function of the personal preferences of the user of the control system.

In an especially preferred variant of the above embodiment, the processing unit is further configured to output an additional fresh gas correction signal at the fresh gas regulation unit as soon as the determined current end tidal anesthetic concentration in the breathing gas circuit exceeds the maximum end tidal anesthetic concentration to be provided, and wherein the fresh gas regulation unit is further configured to reduce the originally predefined volume flow curve correspondingly in response to this additional fresh gas correction signal. It is advantageously ensured in this variant that the maximum end tidal anesthetic concentration to be provided cannot be exceeded. The user of the control system can consequently leave the anesthesia device unsupervised for a certain period of time, without there being the risk that a dispensing of anesthetic that could be harmful to health could occur. The additional fresh gas correction signal can in this case be outputted at the fresh gas regulation unit regardless of the fresh gas correction signal. In another alternative or additional embodiment, the fresh gas regulation unit is configured to receive the limit concentration signal and to select the predefined volume flow curve from a number of predefined volume flow curves based on the limit concentration signal. In this case, a predefined volume flow curve is selected, which does not exceed the inputted maximum end tidal anesthetic concentration to be provided.

In another embodiment, the processing unit is configured to calculate an expected target duration based on the preset curve, wherein the target duration indicates the duration, after which an end tidal anesthetic concentration is reached in view of the calculated future curve. Consequently, a user of the control system can estimate already at the beginning of an anesthesia after what time the end tidal anesthetic target concentration will be reached. This makes it possible to estimate in a reliable manner how often in the next minutes the control system shall be monitored by the user of the control system. In addition to the expected target duration, the duration until reaching certain predefined intermediate values of the end tidal anesthetic concentration is preferably outputted. As a result, a precise timing of the entire anesthesia process can already take place at the beginning of the anesthesia, namely after activation of the assistance mode according to the present invention.

In another embodiment, the processing unit is further configured to determine the surrounding range of the future curve such that this surrounding range comprises the anesthetic concentrations, which deviate by less than 10%, preferably by less than 5% from the calculated future curve. Such a surrounding range is especially advantageous since a constant correction via the fresh gas correction signal is avoided and yet a relatively precise adherence to the preset curve is ensured. In an alternative embodiment, the surrounding range of the future curve is determined such that it comprises the anesthetic concentrations which deviate by less than 0.5 vol. %, preferably by less than 0.2 vol. % from the calculated future curve.

The control unit according to the present invention is preferably further configured to maintain an oxygen content of the fresh gas within a predefined oxygen range, which oxygen content is to be provided to the person to be treated. This oxygen range is typically in a range between 60 vol. % and 80 vol. %. As is known, the oxygen content is controlled via the control of the quantity of air within the fresh gas. The fresh gas preferably consists of a mixture of air and pure oxygen, so that with a reduction of the air an increase in the oxygen content in the fresh gas can also be achieved. Such a control of the oxygen content for anesthesia devices is known and will not be explained in detail below.

According to a second aspect of the present invention, an anesthesia device with a control system in accordance with at least one of the above embodiments is proposed for accomplishing the object according to the present invention.

The anesthesia device according to the present invention with the control system according to the present invention also comprises all the advantages of this control system. In particular, an especially reliable prediction of the expected future curve of the end tidal anesthetic concentration is ensured.

Furthermore, such an anesthesia device advantageously makes it possible to control the dispensing of fresh gas in an automated manner for setting the end tidal anesthetic concentration, without the anesthetic-dispensing unit having to be actuated in an automated manner. Thus, a manual setting of the provided dosage of the anesthetic is possible, as a result of which health risks because of an excessively high dosage of the anesthetic, for example, due to a malfunction of the control system are avoided.

According to a third aspect of the present invention, a process for controlling the dispensing of fresh gas for an anesthesia device, which has the steps shown below:

Provision of a patient gas-measuring unit, of an anesthetic-dispensing unit, of a user interface, of a fresh gas regulation unit and of a processing unit, wherein the patient gas-measuring unit is to be arranged in a breathing gas circuit of the anesthesia device;

inputting of a user input via the user interface and outputting of a corresponding assistance signal in case of activation of an assistance mode;

continuous determination of an end tidal anesthetic concentration in the breathing gas circuit by the patient gas-measuring unit and outputting of a corresponding measured signal at regular time intervals;

receiving of the assistance signal by the fresh gas regulation unit, regulation of a reduction of a volume flow of a fresh gas that is continuously fed to the breathing gas circuit over time corresponding to a predefined volume flow curve in case of an activation of the assistance mode, which activation is indicated by the assistance signal, and outputting of a fresh gas signal, which indicates the current volume flow of the continuously fed fresh gas;

receiving of the assistance signal, of the measured signal and the fresh gas signal by the processing unit and determination of the current volume flow and of the corresponding, currently measured end tidal anesthetic concentration;

calculation of an expected future curve of the end tidal anesthetic concentration over time based on the current volume flow and on the currently measured end tidal anesthetic concentration in case there is a transition from deactivated assistance mode to activated assistance mode; and outputting and storage of the future curve as preset curve;

outputting of a fresh gas correction signal as soon as the determined current end tidal anesthetic concentration in the breathing gas circuit leaves a surrounding range formed around the preset curve; and changing of the predefined volume flow curve as a function of the fresh gas correction signal, wherein the volume flow of the continuously fed fresh gas is increased when the surrounding range is undershot and is reduced when the surrounding range is exceeded compared to the originally predefined volume flow curve;

is proposed for accomplishing the object according to the present invention.

The last two steps are always carried out during the anesthesia if the anesthetic concentration leaves the surrounding range. The other steps are each carried out once within the framework of the process according to the present invention. In case the assistance mode is deactivated in the meantime, the process according to the present invention starts again with the activation of the assistance mode via the user input.

Preferred embodiments of the process according to the present invention will be described below.

In an especially preferred embodiment, the process according to the present invention further has the following steps Receiving of a fresh gas input and outputting of a corresponding fresh gas regulation signal, wherein the fresh gas input comprises information about a minimal volume flow of the fresh gas to be fed to the breathing gas circuit, which minimal volume flow is to be provided by the fresh gas regulation unit; and receiving of the fresh gas regulation signal and selection of the predefined volume flow curve from a number of predefined volume flow curves based on the fresh gas regulation signal.

It is advantageously ensured within the framework of this embodiment that individual experiences and preferences with regard to the desired volume flow curve can be taken into consideration when using an anesthesia device according to the present invention. In this case, the minimal volume flow of the fresh gas represents a parameter, on which the user of the anesthesia device typically has an opinion with regard to an ideal value in this respect, which opinion is empirically substantiated from the user's daily practice. The settability of an individual value is therefore especially advantageous.

According to another embodiment, the process according to the present invention further has the steps Receiving of a limit concentration input and outputting of a corresponding limit concentration signal to the processing unit, wherein the limit concentration input comprises information about a maximum end tidal anesthetic concentration to be provided to a patient to be treated by the anesthesia device; and outputting of an additional fresh gas correction signal as soon as the defined current end tidal anesthetic concentration in the breathing gas circuit exceeds the maximum end tidal anesthetic concentration to be provided, wherein the originally predefined volume flow curve is correspondingly reduced in response to this additional fresh gas correction signal.

In this embodiment, it is advantageously ensured that the end tidal anesthetic concentration cannot exceed a predefined limit value. Consequently, the risk of damage to health because of an excessively high dosage of the anesthetic is avoided. Thus, the process according to the present invention according to this embodiment represents an especially safe process for controlling the dispensing of fresh gas.

The present invention shall now be explained in more detail on the basis of advantageous exemplary embodiments, which are schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
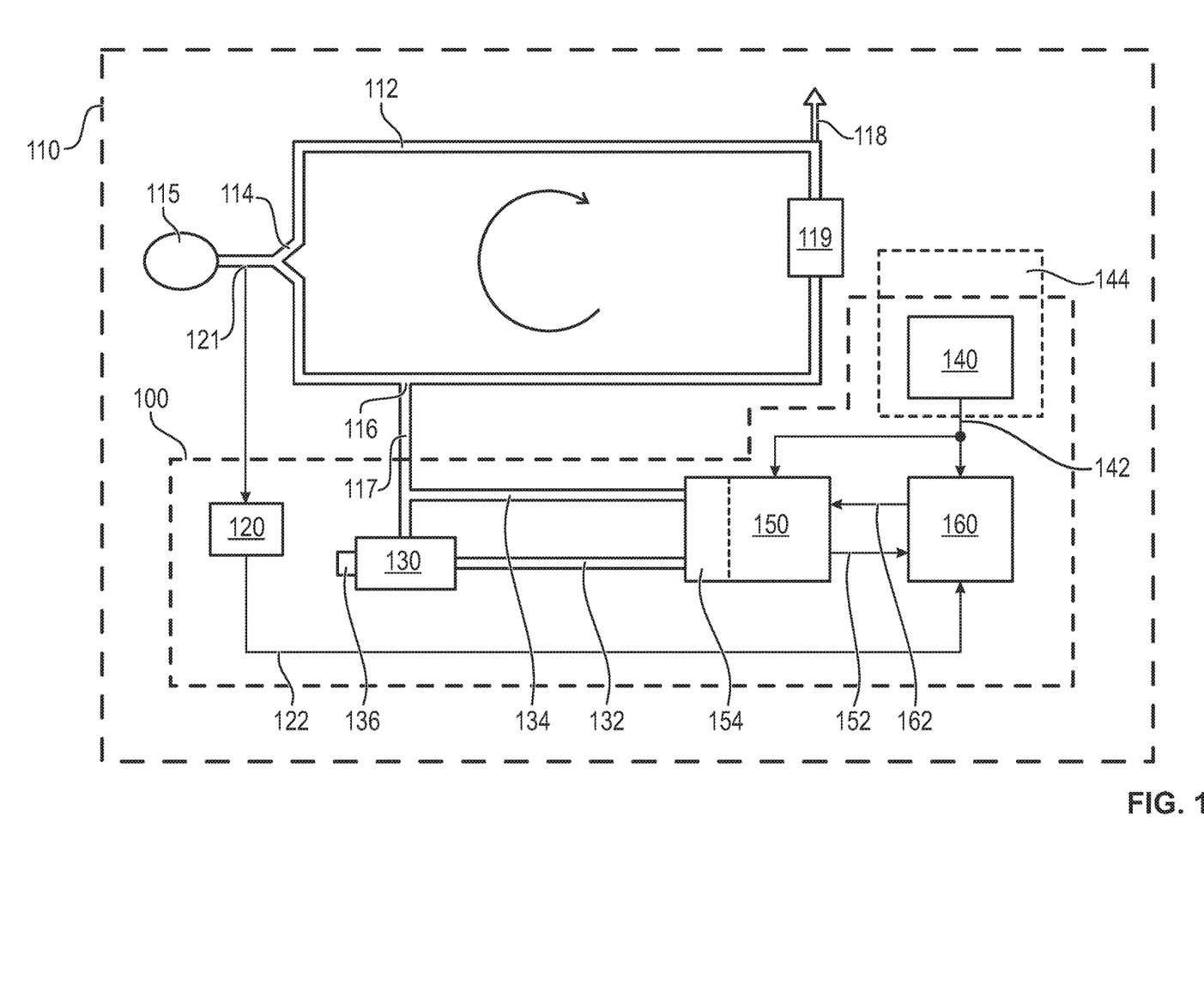
FIG. 1 is a schematic view of a first exemplary embodiment of the control system according to the present invention according to the first aspect of the present invention.

Referring to the drawings, FIG. 1 shows a schematic view of a first exemplary embodiment of the control system 100 according to the present invention according to the first aspect of the present invention.

The control system 100 is configured to control the dispensing of fresh gas for an anesthesia device 110 and comprises at least one patient gas-measuring unit 120, an anesthetic-dispensing unit 130, a user interface 140, a fresh gas regulation unit 150 and a processing unit 160. The at least one patient gas-measuring unit 120 is arranged in a breathing gas circuit 112 of the anesthesia device 110. In the present embodiment, the patient gas-measuring unit 120 is arranged in the area of a Y-piece 114 of the breathing gas circuit 112 and thus close to the person to be supplied with anesthetic. By contrast, an inlet 116 of the fresh gas 117 is arranged in the breathing gas circuit 112 at a spaced location from the person 115. Furthermore, the breathing gas circuit 112 has on its end-expiratory side a valve 118 for regulating the gas volume within the breathing gas circuit 112 and a $CO_2$ absorber 119 for reducing the carbon dioxide content in the inhaled air provided by the anesthesia device 110.

The patient gas-measuring unit 120 according to the present invention is configured to determine an end tidal anesthetic concentration in the breathing gas circuit and to output a corresponding measured signal 122 at regular time intervals. In this connection, the measured signal 122 is cable-based or sent via a wireless connection to the processing unit 160.

The anesthetic-dispensing unit 130 is configured to make it possible to dispense an anesthetic in a fresh gas 117 being fed to the breathing gas circuit 112. The anesthetic-dispensing unit 130 is connected in this case directly via a first fresh gas line 132 to the fresh gas regulation unit 150. In addition to the first fresh gas line 132, a second fresh gas line 134, which bypasses the anesthetic-dispensing unit 130, leads directly to the inlet 116 of the fresh gas 117. In the exemplary embodiment shown, the anesthetic-dispensing unit 130 is a manually controlled anesthetic-dispensing unit configured to dispense the anesthetic in an exclusively manually controlled manner. This is achieved via a control element 136 to be operated manually in the present embodiment.

The user interface 140 is configured to activate and to deactivate an assistance mode of the control system and to output a corresponding assistance signal 142 if a corresponding user input is present. The user input is carried out in the exemplary embodiment shown by pressing a corresponding button at the user interface 140. After an activation, the assistance mode can be deactivated by pressing this button again, which in turn leads to the output of a corresponding assistance signal 142. In the exemplary embodiment shown, the user interface 140 is part of a general input unit 144 of the anesthesia device 110 in question.

The fresh gas regulation unit 150 is arranged and configured to receive the assistance signal 142 and when the assistance mode is activated, to regulate a reduction of a volume flow of the continuously fed fresh gas 117 over time corresponding to a predefined volume flow curve. Furthermore, the fresh gas regulation unit 150 is configured to output at regular time intervals a fresh gas signal 152, which indicates the current volume flow of the continuously fed fresh gas. In the present embodiment, the fresh gas regulation unit 150 is integrated directly into a fresh gas supply unit 154, namely into an $O_2$ supply unit and into an air supply unit. In an exemplary embodiment, not shown, the fresh gas provided also comprises $N_2O$. The predefined volume flow curve is a curve, which comprises a continuous, degressive reduction of the volume flow of the fresh gas over time. In this case, the predefined volume flow curve is selected such that it begins in an area of the currently provided volume flow, so that no abrupt change in the volume flow takes place when the assistance mode is activated.

The processing unit 160 is configured to receive the measured signal 122 and the fresh gas signal 152 and to determine therefrom the current volume flow of the fed fresh gas and the current end tidal anesthetic concentration in the breathing gas circuit. Furthermore, the processing unit 160 is configured to receive the assistance signal 142 and to calculate an expected future curve of the end tidal anesthetic concentration over time when there is a transition from deactivated assistance mode to activated assistance mode based on the current volume flow, on the predefined volume flow curve and on the current end tidal anesthetic concentration, to output the calculated expected future curve as a preset curve and to store the preset curve. The predefined volume flow curve is transmitted in this case via the fresh gas signal 152 or is available to the processing unit 160 by an internal memory. In this case, the processing unit is further configured to output a fresh gas correction signal 162 at the fresh gas regulation unit as soon as the determined current end tidal anesthetic concentration in the breathing gas circuit 112 leaves a surrounding range of the preset curve, which surrounding range is formed around the preset curve. That is, the surrounding range is a range of anesthetic concentrations between an upper threshold curve that follows the calculated expected future curve at a preset value higher than the calculated expected future curve and a lower threshold curve that follows the calculated expected future curve at a preset value lower than the calculated expected future curve. The surrounding range is formed around the preset curve in the exemplary embodiment shown such that the surrounding range comprises the anesthetic concentrations, which deviate by less than 10%, preferably by less than 5% from the calculated expected future curve (preset curve). In an exemplary embodiment, not shown, the surrounding range is selected such that the surrounding range comprises the anesthetic concentrations, which deviate by less than 0.5 vol. %, preferably by less than 0.2 vol. % from the calculated future curve.

Furthermore, the fresh gas regulation unit 150 is configured to receive the fresh gas correction signal 162 to change the predefined volume flow curve as a function of the fresh gas correction signal 162, wherein the volume flow of the continuously fed fresh gas 117 is increased when the surrounding range is undershot and is reduced when the surrounding range is exceeded compared to the originally predefined volume flow curve.

In the present embodiment, sevoflurane is used as anesthetic; however, the control system according to the present invention can be implemented with any kind of anesthetic.

FIG. 1 does not show all elements of a typical breathing gas circuit, as it is usually present when using an anesthesia device. Such typical elements are generally known and are not essential for the control system according to the present invention, so that these will not be further discussed here.

In an exemplary embodiment, not shown, the control system according to the present invention comprises two patient gas-measuring units, which determine the end tidal anesthetic concentration parallel to one another. Consequently, a defect of the patient gas-measuring unit can be detected especially rapidly and, in addition, in an automated manner.

Figure 2:
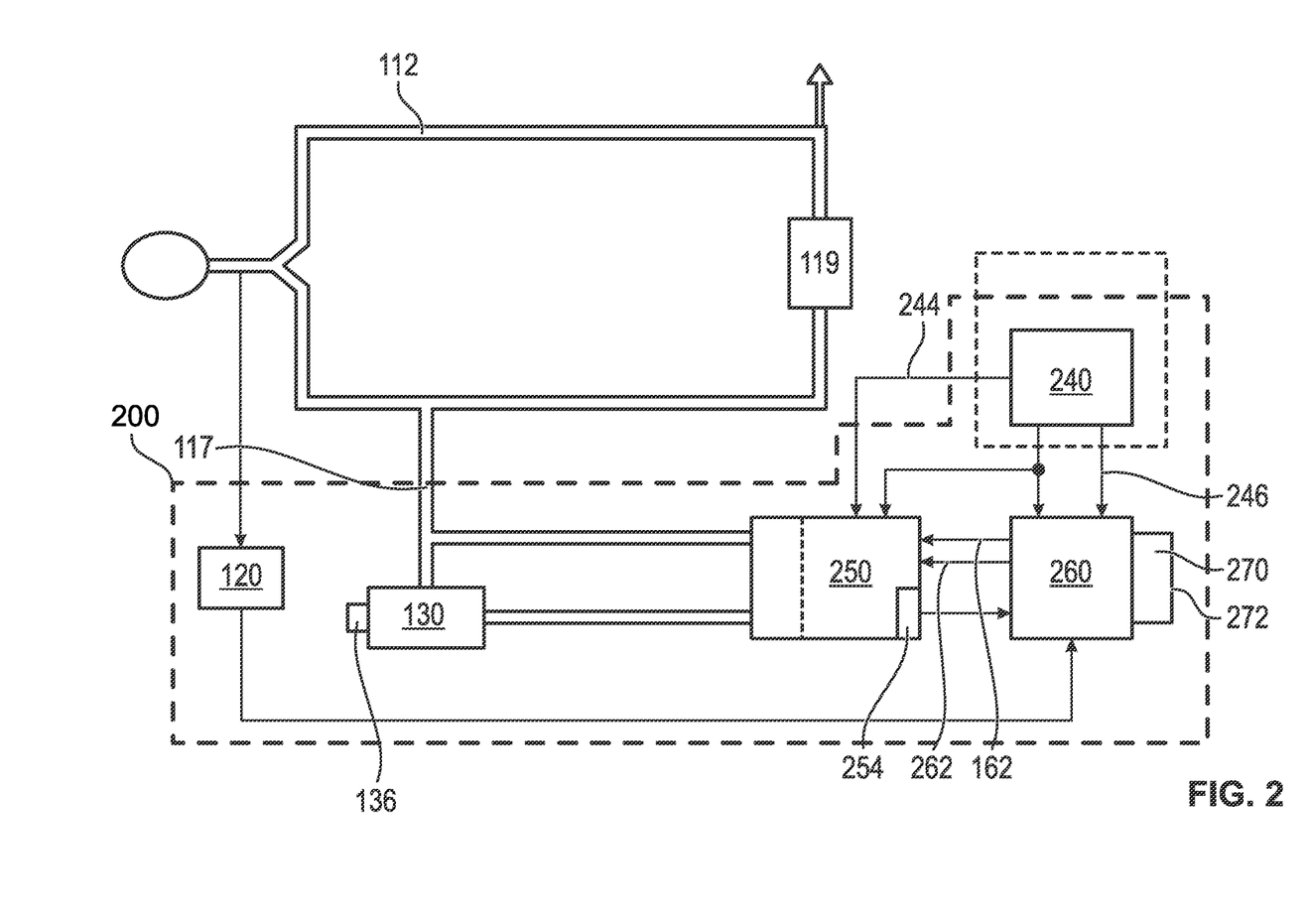
FIG. 2 is a schematic view of a second exemplary embodiment of the control system according to the present invention according to the first aspect of the present invention.

FIG. 2 shows a schematic view of a second exemplary embodiment of the control system 200 according to the present invention according to the first aspect of the present invention.

The control system 200 differs from the control system 100 shown in FIG. 1 by further having an output unit 270.

The output unit 270 is signal connected to the processing unit 260 and is configured to output the preset curve as a graphic view with the calculated expected future curve of the end tidal anesthetic concentration over time. In this case, the graphic output is carried out on a display 272 of the output unit 270. In addition to the graphic output, the expected duration, after which a preset end tidal anesthetic target concentration is reached in view of the calculated future curve, is also indicated in the exemplary embodiment being shown.

In an exemplary embodiment, not shown, the output of the future curve is carried out via the output of predefined characteristic parameters of this future curve.

Furthermore, the control system 200 differs from the control system 100 by the user interface 240 being configured to receive a fresh gas input and to output a corresponding fresh gas regulation signal 244. In this case, the fresh gas input comprises information about a minimal volume flow of the fresh gas 117 to be fed to the breathing gas circuit 112, which minimal volume flow is to be provided by the fresh gas regulation unit. The used volume flow of the fresh gas, for example, for sevoflurane, is typically in a range between 300 mL/min and 8 L/min. The individually set, minimal volume flow will therefore be in a range between 300 mL/min and 1 L/min. In the present embodiment, the control system is configured not to allow any input of a minimal volume flow of less than 250 mL/min. 250 mL/min is the physiological minimum of the fresh gas to be provided regardless of the anesthetic being used.

The fresh gas regulation unit 250 is in turn configured to receive the fresh gas regulation signal 244 and to select the predefined volume flow curve from a number of predefined volume flow curves based on the fresh gas regulation signal 244. The number of predefined volume flow curves is stored in a memory unit 254 integrated into the fresh gas regulation unit 250.

In an exemplary embodiment, not shown, the processing unit is configured to receive the fresh gas regulation signal and to output a warning signal when the inputted minimal volume flow is reached.

Finally, the user interface 240 is additionally configured to receive a limit concentration input and to output a corresponding limit concentration signal 246 at the processing unit. In this case, the limit concentration input indicates how high the maximum end tidal anesthetic concentration may be. The anesthetic concentration is typically maintained between 3 vol. % and 8 vol. % within the framework of the anesthesia. The limit concentration input will therefore preferably be in a range between 8 vol. % and 12 vol. %, depending on in which area a user of the control system according to the present invention would preferably like to work.

The processing unit 260 will in turn output a corresponding, additional fresh gas correction signal 262 at the fresh gas regulation unit 250 as soon as the determined current end tidal anesthetic concentration in the breathing gas circuit exceeds the maximum end tidal anesthetic concentration to be provided. The originally predefined volume flow curve will correspondingly be reduced by the fresh gas regulation unit 250 as a response to this additional fresh gas correction signal 262. The originally predefined volume flow curve is defined as the predefined volume flow curve, which has been set after the last fresh gas correction signal 162, 262 or which has been set after activation of the assistance mode in case no fresh gas correction signal 162, 262 was outputted.

Figure 3:
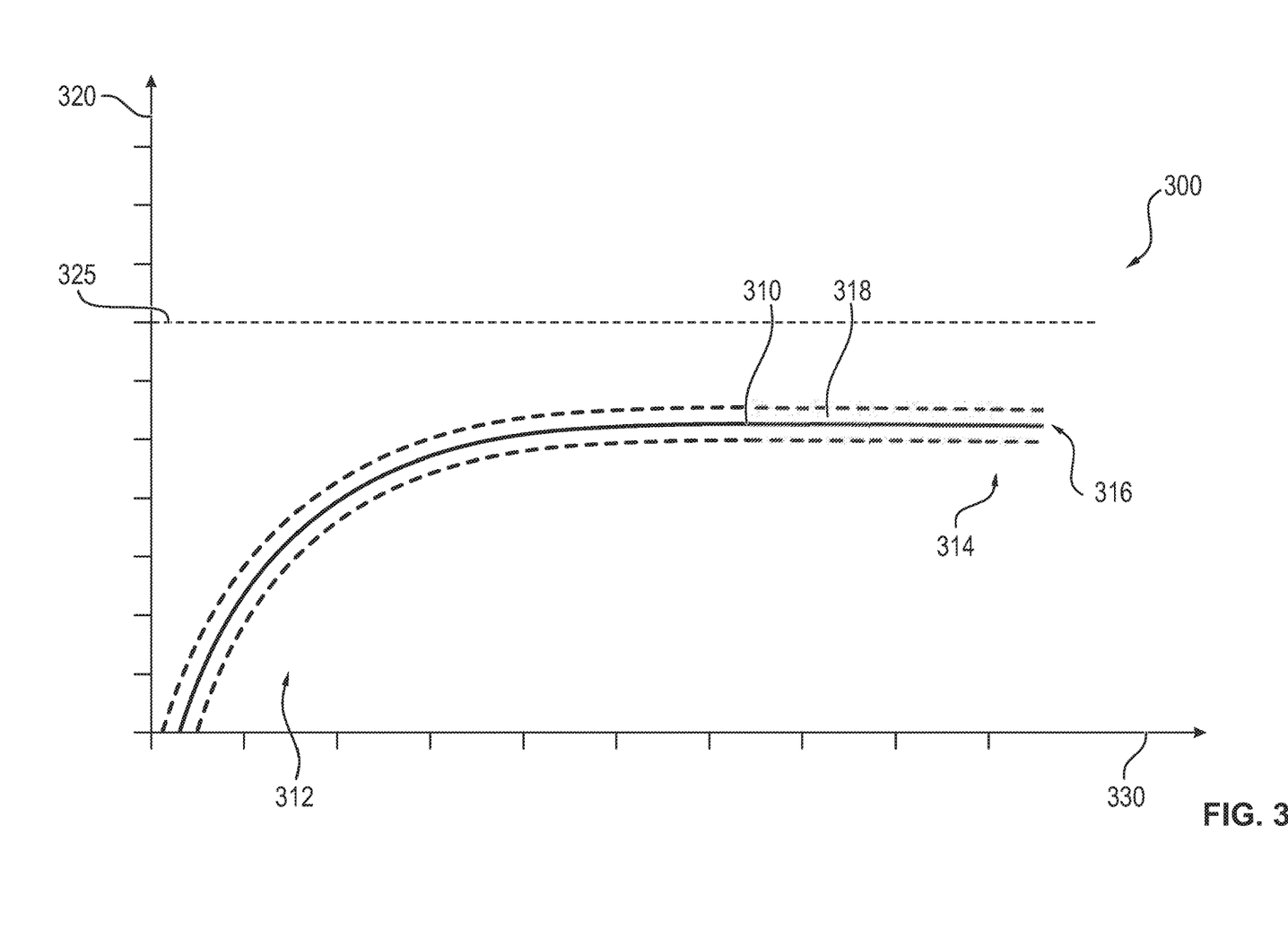
FIG. 3 is an illustration of a graphic output of a preset curve of a control system according to the first aspect of the present invention.

FIG. 3 shows an illustration of a graphic output 300 of a preset curve 310 of a control system according to the first aspect of the present invention.

The graphic output 300 shows a diagram, the ordinate 320 of which indicates the end tidal anesthetic concentration in vol. %. Furthermore, the limit concentration 325, i.e., the manually set or predefined maximum end tidal anesthetic concentration, is indicated on the ordinate.

The abscissa 330 of the graphic output 300 indicates the time in minutes since the beginning of the anesthesia process. In an alternative exemplary embodiment, not shown, the graphic output indicates the time since the beginning of the activation of the assistance mode.

In the example of the preset curve 310 shown, the assistance mode was already activated at the beginning of the anesthesia process. The typical curve of such a preset curve 310 comprises here a beginning area 312 with a rapid increase of the end tidal anesthetic concentration, which corresponds to an initially large volume flow of the fresh gas (see FIG. 4 for this). After the beginning area 312, a target area 314 is set, in which the end tidal anesthetic concentration is in the range of a desired end tidal anesthetic target concentration.

The surrounding range 318, which comprises the anesthetic concentrations, which deviate by less than 0.5 vol. % from the preset curve 310, is formed around the preset curve 310.

In one exemplary embodiment, not shown, the actually measured curve of the anesthetic concentration is additionally indicated, which cannot be outside of the surrounding range because of the automated control via the fresh gas correction according to the present invention.

Figure 4:
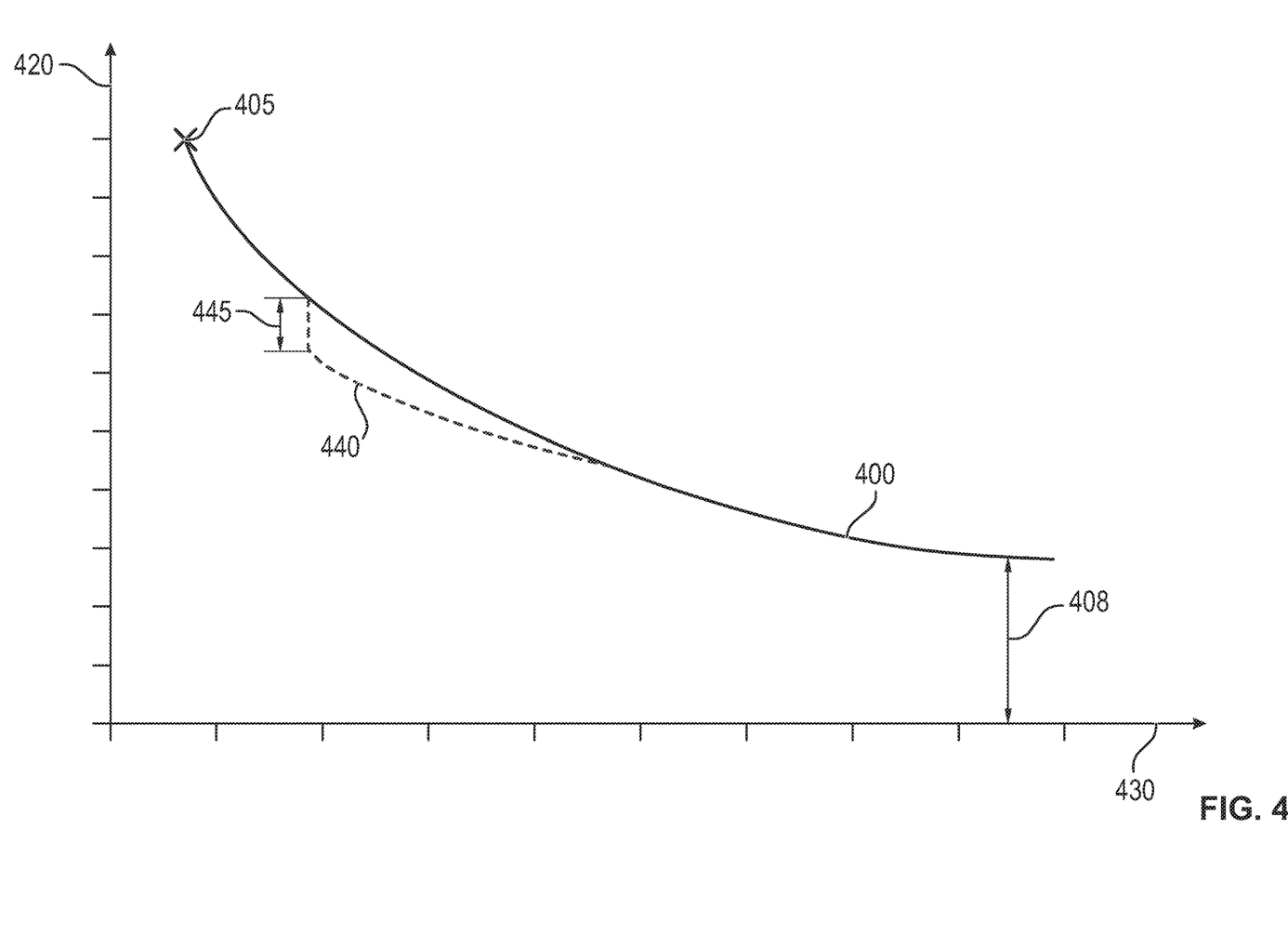
FIG. 4 is an illustration of a predefined volume flow curve processed within a control system according to the present invention according to the first aspect of the present invention.

FIG. 4 shows an illustration of a predefined volume flow curve 400 processed within a control system according to the present invention.

The illustration shows here a diagram, wherein a volume flow in L/min is plotted over the ordinate 420 and the time in minutes is plotted over the abscissa 430.

The volume flow curve 400 begins with a starting volume flow 405, which is present on activation of the assistance mode. Starting from there, the predefined volume flow curve 400 is predefined by the fresh gas regulation unit. In the present embodiment, the predefined volume flow curve 400 was determined here based on a minimal volume flow 408 of the fresh gas to be fed to the breathing gas circuit, which minimal volume flow is inputted by the user of the control system.

Likewise shown by dotted lines in FIG. 4 is a changed predefined volume flow curve 440, which results due to a reduction 445 of the originally predefined volume flow curve 400. The step in the changed predefined volume flow curve 440, which step was caused by the fresh gas correction signal, can be seen. Such a reduction 445 would take place according to the present invention, for example, in case the current end tidal anesthetic concentration exceeds the surrounding range. The continuous, degressive reduction of the volume flow 400, 440 over time that is otherwise achieved can, furthermore, be seen.

The shown reduction 445 and the corresponding changed volume flow curve 440 are only shown as examples. In other exemplary embodiments, not shown, the magnitude of the change and/or the curve of the changed volume flow hereof have different configurations.

Figure 5:
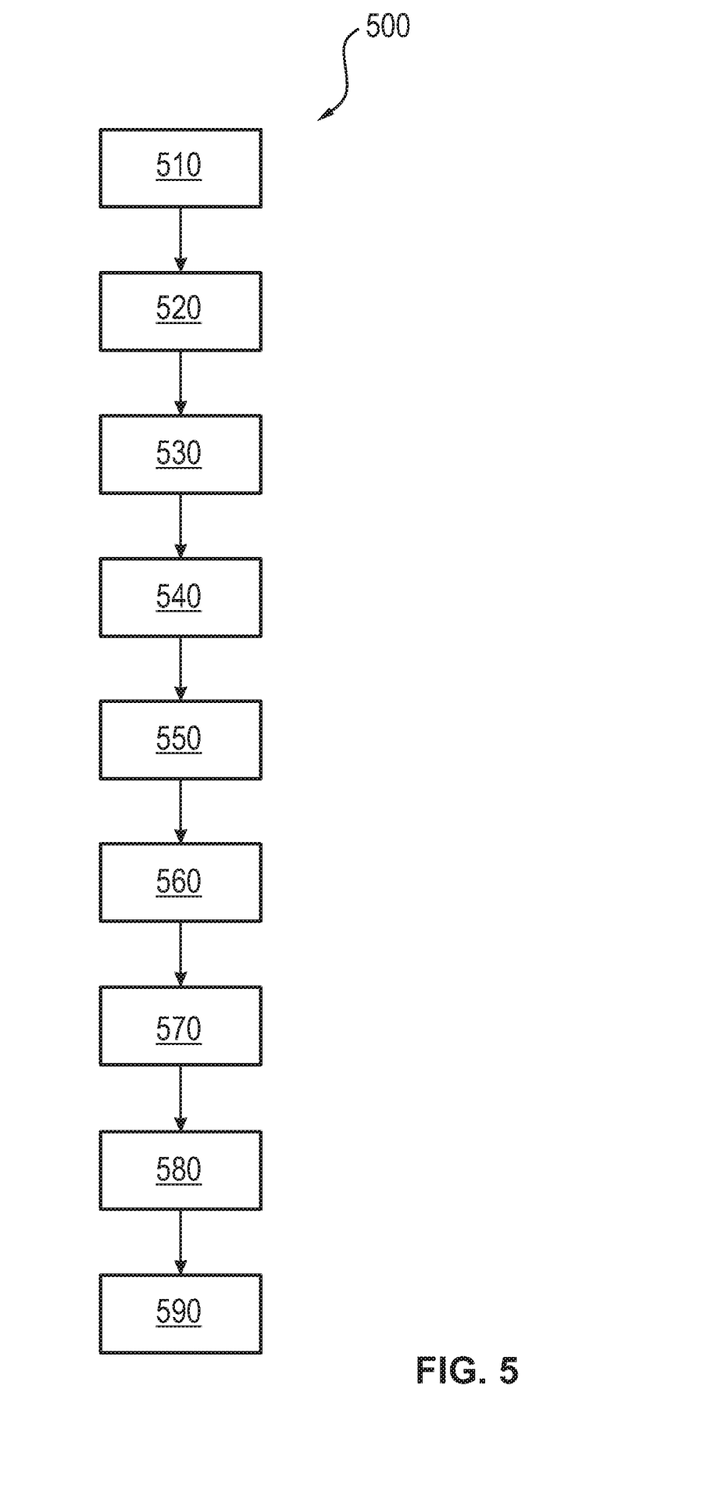
FIG. 5 is a flow chart of a first exemplary embodiment of the process according to the present invention according to the third aspect of the present invention.

FIG. 5 shows a flow chart 500 of a first exemplary embodiment of the process according to the present invention according to the third aspect of the present invention.

The process 500 according to the present invention for controlling the dispensing of fresh gas for an anesthesia device has the steps 510, 520, 530, 540, 550, 560, 570, 580, 590 explained below.

A first step 510 comprises a provision of a patient gas-measuring unit, of an anesthetic-dispensing unit, of a user interface, of a fresh gas regulation unit and of a processing unit, wherein the patient gas-measuring unit is to be arranged in a breathing gas circuit of the anesthesia device.

A next step 520 comprises an input of a user input via the user interface and an output of a corresponding assistance signal in case an assistance mode is activated.

A further step 530 comprises a continuous determination of an end tidal anesthetic concentration in the breathing gas circuit by the patient gas-measuring unit and an outputting of a corresponding measured signal at regular time intervals.

A next step 540 comprises the receiving of the assistance signal by the fresh gas regulation unit, a regulation of a reduction of a volume flow of a fresh gas continuously fed to the breathing gas circuit over time corresponding to a predefined volume flow curve in case of an activation of the assistance mode, which activation is indicated by the assistance signal, and an outputting of a fresh gas signal, which indicates the current volume flow of the continuously fed fresh gas.

A further step 550 comprises a receiving of the assistance signal, of the measured signal and of the fresh gas signal by the processing unit and a determination of the current volume flow and of the corresponding currently measured end tidal anesthetic concentration.

A next step 560 comprises a calculation of an expected future curve of the end tidal anesthetic concentration over time based on the current volume flow and on the currently measured end tidal anesthetic concentration in case there is a transition from deactivated assistance mode to activated assistance mode.

In a step 570 subsequent thereto, the future curve is outputted and stored as preset curve.

A next step 580 comprises an outputting of a fresh gas correction signal as soon as the determined current end tidal anesthetic concentration in the breathing gas circuit leaves a surrounding range formed around the preset curve.

The final step 590 comprises a changing of the predefined volume flow curve as a function of the fresh gas correction signal, wherein the volume flow of the continuously fed fresh gas is increased when the surrounding range is undershot and is reduced when the surrounding range is exceeded compared to the originally predefined volume flow curve.

Step 510 is typically carried out before a first anesthesia process and retained unchanged thereafter via a plurality of anesthesia processes.

Steps 580 and 590 are carried out in case the surrounding range is left and a corresponding actuation of the fresh gas volume by the fresh gas correction signal becomes necessary according to the present invention. Hence, these steps may also take place multiple times within a single anesthesia process.

It is especially advantageous that the process according to the present invention can be carried out without a control of the anesthetic-dispensing unit, since the concentration of the anesthetic no longer has to be changed after an initial, for example, manual setting, since the control according to the present invention already operates with exclusive fresh air control.

While specific embodiments of the invention have been shown and described in detail to illustrate the application of the principles of the invention, it will be understood that the invention may be embodied otherwise without departing from such principles.

LIST OF REFERENCE NUMBERS

100, 200 Control system
110 Anesthesia device
112 Breathing gas circuit
114 Y-piece
115 Person
116 Inlet
117 Fresh gas
118 Valve
119 $CO_2$ absorber
120 Patient gas-measuring unit
122 Measured signal
130 Anesthetic-dispensing unit
132 First fresh gas line
134 Second fresh gas line
136 Control element to be operated manually
140, 240 User interface
142 Activation signal
144 General input unit
150, 250 Fresh gas regulation unit
152 Fresh gas signal
154 Fresh gas supply unit
160, 260 Processing unit
162 Fresh gas correction signal
244 Fresh gas regulation signal
246 Limit concentration signal
254 Integrated memory unit
262 Additional fresh gas correction signal
270 Output unit
272 Display
300 Graphic output
310 Preset curve
312 Beginning area
314 Target area
316 End tidal anesthetic target concentration
318 Surrounding range
320, 420 Ordinate
325 Limit concentration
330, 430 Abscissa
400 Predefined volume flow curve
405 Starting volume flow
408 Inputted minimal volume flow
440 Changed predefined volume flow curve
445 Reduction
500 Process
510, 520, 530, 540, 550 Process steps
560, 570 580, 590

What is claimed is:

1. A control system for controlling a dispensing of a fresh gas for an anesthesia device, the control system comprising:
   a gas measuring unit arranged in a breathing gas circuit of the anesthesia device and configured to determine an end tidal anesthetic concentration in the breathing gas circuit and to output a corresponding measured signal at regular time intervals;
   an anesthetic dispensing unit configured to dispense an anesthetic in a fresh gas being fed to the breathing gas circuit;
   a user interface configured to activate or deactivate an assistance mode of the control system when a corresponding user input is present and to output a corresponding assistance signal;
   a fresh gas regulation unit arranged and configured to receive the assistance signal and, upon the assistance mode being activated, to regulate a reduction of a volume flow of the continuously fed fresh gas over time corresponding to a predefined volume flow curve, and to output a fresh gas signal at regular time intervals that indicates a current volume flow of the continuously fed fresh gas; and
   a processing unit configured to receive the measured signal and the fresh gas signal and to determine therefrom the current volume flow of the fed fresh gas and the current end tidal anesthetic concentration in the breathing gas circuit and to receive the assistance signal and, upon the assistance signal indicating a transition from a deactivated assistance mode to an activated assistance mode based on the current volume flow, the predefined volume flow curve and the current end tidal anesthetic concentration, to calculate an expected future curve of the end tidal anesthetic concentration over time, and to output the expected future curve of the end tidal anesthetic concentration over time as a preset curve and to store the preset curve, wherein:

the processing unit is further configured to output a fresh gas correction signal at the fresh gas regulation unit as soon as the defined current end tidal anesthetic concentration in the breathing gas circuit leaves a surrounding range of the preset curve, which surrounding range is formed around the preset curve; and the fresh gas regulation unit is further configured to receive the fresh gas correction signal and to change the predefined volume flow curve as a function of the fresh gas correction signal and to increase the volume flow of the continuously fed fresh gas upon the surrounding range being undershot and to reduce the volume flow of the continuously fed fresh gas when the surrounding range is exceeded compared to the predefined volume flow curve prior to the change, wherein the predefined volume flow curve comprises a degressive reduction of the volume flow over time.

2. A control system in accordance with claim 1, further comprising an output unit signal connected to the processing unit, the output unit being configured to output the preset curve with the calculated expected future curve of the end tidal anesthetic concentration over time as a graphic view.

3. A control system in accordance with claim 1, wherein the anesthetic dispensing unit is a manually controlled anesthetic dispensing unit configured to exclusively dispense anesthetic under manual control.

4. A control system in accordance with claim 1, wherein:
the user interface is further configured to receive a fresh gas input and to output a corresponding fresh gas regulation signal; and
the fresh gas input comprises information about a minimal volume flow of the fresh gas to be fed to the breathing gas circuit, which minimal volume flow is to be provided by means of the fresh gas regulation unit.

5. A control system in accordance with claim 4, wherein the fresh gas regulation unit is further configured to receive the fresh gas regulation signal and to select the predefined volume flow curve from a number of predefined volume flow curves based on the fresh gas regulation signal.

6. A control system in accordance with claim 1, wherein:
the user interface is further configured to receive a limit concentration input and to output a corresponding limit concentration signal to the processing unit; and
the limit concentration input comprises information about a maximum end tidal anesthetic concentration to be provided to a patient to be supplied by the anesthesia device.

7. A control system in accordance with claim 6, wherein:
the processing unit is further configured to output an additional fresh gas correction signal to the fresh gas regulation unit as soon as the defined current end tidal anesthetic concentration in the breathing gas circuit exceeds the maximum end tidal anesthetic concentration to be provided; and
the fresh gas regulation unit is further configured to reduce the originally predefined volume flow curve corresponding to the to the additional fresh gas correction signal, in response to the additional fresh gas correction signal.

8. An anesthesia device comprising a control system for controlling a dispensing of a fresh gas for an anesthesia device, the control system comprising:
a gas measuring unit arranged in a breathing gas circuit of the anesthesia device and configured to determine an end tidal anesthetic concentration in the breathing gas circuit and to output a corresponding measured signal at regular time intervals;

an anesthetic dispensing unit configured to dispense an anesthetic in a fresh gas being fed to the breathing gas circuit;
a user interface configured to activate or deactivate an assistance mode of the control system when a corresponding user input is present and to output a corresponding assistance signal;
a fresh gas regulation unit arranged and configured to receive the assistance signal and, upon the assistance mode being activated, to regulate a reduction of a volume flow of the continuously fed fresh gas over time corresponding to a predefined volume flow curve, and to output a fresh gas signal at regular time intervals that indicates a current volume flow of the continuously fed fresh gas; and
a processing unit configured to receive the measured signal and the fresh gas signal and to determine therefrom the current volume flow of the fed fresh gas and the current end tidal anesthetic concentration in the breathing gas circuit and to receive the assistance signal and, upon the assistance signal indicating a transition from a deactivated assistance mode to an activated assistance mode based on a current volume flow, the predefined volume flow curve and the current end tidal anesthetic concentration, to calculate an expected future curve of the end tidal anesthetic concentration over time, and to output the expected future curve of the end tidal anesthetic concentration over time as a preset curve and to store the preset curve, wherein:
the processing unit is further configured to output a fresh gas correction signal at the fresh gas regulation unit as soon as the defined current end tidal anesthetic concentration in the breathing gas circuit leaves a surrounding range of the preset curve, which surrounding range is formed around the preset curve; and
the fresh gas regulation unit is further configured to receive the fresh gas correction signal and to change the predefined volume flow curve as a function of the fresh gas correction signal and to increase the volume flow of the continuously fed fresh gas upon the surrounding range being undershot and to reduce the volume flow of the continuously fed fresh gas when the surrounding range is exceeded compared to the predefined volume flow curve prior to the change, wherein the predefined volume flow curve comprises a degressive reduction of the volume flow over time.

9. An anesthesia device in accordance with claim 8, wherein: the processing unit is further configured to calculate an expected target duration based on the preset curve; and
the target duration indicates a duration, after which an end tidal anesthetic concentration is reached in view of the calculated expected future curve.

10. An anesthesia device in accordance with claim 8, wherein the processing unit is further configured to determine the surrounding range of the calculated expected future curve such that the determined surrounding range comprises the anesthetic concentrations, which deviate by less than 10% from the calculated expected future curve.

11. An anesthesia device in accordance with claim 8, further comprising an output unit signal connected to the processing unit, the output unit being configured to output the preset curve with the calculated expected future curve of the end tidal anesthetic concentration over time as a graphic view.

12. An anesthesia device in accordance with claim 8, wherein the anesthetic dispensing unit is a manually controlled anesthetic dispensing unit configured to exclusively dispense anesthetic under manual control.

13. An anesthesia device in accordance with claim 8, wherein:
the user interface is further configured to receive a fresh gas input and to output a corresponding fresh gas regulation signal;
the fresh gas input comprises information about a minimal volume flow of the fresh gas to be fed to the breathing gas circuit, which minimal volume flow is to be provided by means of the fresh gas regulation unit; and
the fresh gas regulation unit is further configured to receive the fresh gas regulation signal and to select the predefined volume flow curve from a number of predefined volume flow curves based on the fresh gas regulation signal.

14. An anesthesia device in accordance with claim 8, wherein:
the user interface is further configured to receive a limit concentration input and to output a corresponding limit concentration signal to the processing unit;
the limit concentration input comprises information about a maximum end tidal anesthetic concentration to be provided to a patient to be supplied by the anesthesia device
the processing unit is further configured to output an additional fresh gas correction signal to the fresh gas regulation unit as soon as the defined current end tidal anesthetic concentration in the breathing gas circuit exceeds the maximum end tidal anesthetic concentration to be provided; and
the fresh gas regulation unit is further configured to reduce the originally predefined volume flow curve corresponding to the to the additional fresh gas correction signal, in response to the additional fresh gas correction signal.

15. An anesthesia device in accordance with claim 8, wherein:
the processing unit is further configured to calculate an expected target duration based on the preset curve; and
the target duration indicates a duration, after which an end tidal anesthetic concentration is reached in view of the calculated expected future curve.

16. A control system for controlling a dispensing of a fresh gas for an anesthesia device, the control system comprising:
a gas measuring unit arranged in a breathing gas circuit of the anesthesia device and configured to determine an end tidal anesthetic concentration in the breathing gas circuit and to output a corresponding measured signal at regular time intervals;
an anesthetic dispensing unit configured to dispense an anesthetic in a fresh gas being fed to the breathing gas circuit;
a user interface configured to activate or deactivate an assistance mode of the control system when a corresponding user input is present and to output a corresponding assistance signal;
a fresh gas regulation unit arranged and configured to receive the assistance signal and, upon the assistance mode being activated, to regulate a reduction of a volume flow of the continuously fed fresh gas over time corresponding to a predefined volume flow curve, and to output a fresh gas signal at regular time intervals that indicates a current volume flow of the continuously fed fresh gas; and a processing unit configured to receive the measured signal and the fresh gas signal and to determine therefrom the current volume flow of the fed fresh gas and the current end tidal anesthetic concentration in the breathing gas circuit and to receive the assistance signal and, upon the assistance signal indicating a transition from a deactivated assistance mode to an activated assistance mode, based on the current volume flow, the predefined volume flow curve and the current end tidal anesthetic concentration, to calculate an expected future curve of the end tidal anesthetic concentration over time, and to output the expected future curve of the end tidal anesthetic concentration over time as a preset curve and to store the preset curve, wherein:
the processing unit is further configured to output a fresh gas correction signal at the fresh gas regulation unit as soon as the defined current end tidal anesthetic concentration in the breathing gas circuit leaves a surrounding range of the preset curve, which surrounding range is formed around the preset curve; and
the fresh gas regulation unit is further configured to receive the fresh gas correction signal and to change the predefined volume flow curve as a function of the fresh gas correction signal and to increase the volume flow of the continuously fed fresh gas upon the surrounding range being undershot and to reduce the volume flow of the continuously fed fresh gas when the surrounding range is exceeded compared to the predefined volume flow curve prior to the change, wherein the predefined volume flow curve comprises a continuous, degressive reduction of the volume flow over time.

17. An anesthesia device comprising a control system for controlling a dispensing of a fresh gas for an anesthesia device, the control system comprising:
a gas measuring unit arranged in a breathing gas circuit of the anesthesia device and configured to determine an end tidal anesthetic concentration in the breathing gas circuit and to output a corresponding measured signal at regular time intervals;
an anesthetic dispensing unit configured to dispense an anesthetic in a fresh gas being fed to the breathing gas circuit;
a user interface configured to activate or deactivate an assistance mode of the control system when a corresponding user input is present and to output a corresponding assistance signal;
a fresh gas regulation unit arranged and configured to receive the assistance signal and, upon the assistance mode being activated, to regulate a reduction of a volume flow of the continuously fed fresh gas over time corresponding to a predefined volume flow curve, and to output a fresh gas signal at regular time intervals that indicates a current volume flow of the continuously fed fresh gas; and
a processing unit configured to receive the measured signal and the fresh gas signal and to determine therefrom the current volume flow of the fed fresh gas and the current end tidal anesthetic concentration in the breathing gas circuit and to receive the assistance signal and, upon the assistance signal indicating a transition from a deactivated assistance mode to an activated assistance mode based on a current volume flow, the predefined volume flow curve and the current end tidal anesthetic concentration, to calculate an expected future curve of the end tidal anesthetic concentration over time, and to output the expected future curve of the end tidal anesthetic concentration over time as a preset curve and to store the preset curve, wherein:

the processing unit is further configured to output a fresh gas correction signal at the fresh gas regulation unit as soon as the defined current end tidal anesthetic concentration in the breathing gas circuit leaves a surrounding range of the preset curve, which surrounding range is formed around the preset curve; and the fresh gas regulation unit is further configured to receive the fresh gas correction signal and to change the predefined volume flow curve as a function of the fresh gas correction signal and to increase the volume flow of the continuously fed fresh gas upon the surrounding range being undershot and to reduce the volume flow of the continuously fed fresh gas when the surrounding range is exceeded compared to the predefined volume flow curve prior to the change, wherein the predefined volume flow curve comprises a continuous, degressive reduction of the volume flow over time.

18. A process for controlling a dispensing of a fresh gas for an anesthesia device, the process comprising the steps of:

providing a patient gas measuring unit, of the anesthetic dispensing unit, wherein the patient gas measuring unit is arranged in a breathing gas circuit of the anesthesia device;

providing a user interface, a fresh gas regulation unit and a processing unit;

inputting a user input via the user interface and outputting a corresponding assistance signal in case of activation of an assistance mode via said user input;

continuously determining an end tidal anesthetic concentration in the breathing gas circuit by the patient gas measuring unit and outputting a corresponding measured signal at regular time intervals;

receiving the assistance signal by the fresh gas regulation unit and regulating a reduction of a volume flow of a fresh gas that is continuously fed to the breathing gas circuit over time corresponding to a predefined volume flow curve in case of activation of the assistance mode which activation is indicated by the assistance signal, and outputting a fresh gas signal, which indicates a current volume flow of the continuously fed fresh gas;

receiving the assistance signal, of the measured signal and of the fresh gas signal by the processing unit and with the processing unit determining a current volume flow corresponding currently measured end tidal anesthetic concentration;

calculating an expected future curve of the end tidal anesthetic concentration over time based on the current volume flow and the currently measured end tidal anesthetic concentration in case a transition from deactivated assistance mode to activated assistance mode is present;

outputting and storing the future curve as a preset curve;

outputting a fresh gas correction signal upon the determined current end tidal anesthetic concentration in the breathing gas circuit leaving a surrounding range of the preset curve; and changing the predefined volume flow curve as a function of the fresh gas correction signal, wherein the volume flow of the continuously fed fresh gas is increased when the surrounding range is undershot and is reduced when the surrounding range is exceeded compared to the originally predefined volume flow curve, wherein the predefined volume flow curve comprises a degressive reduction of the volume flow over time.

19. A process in accordance with claim 18, further comprising the steps of:

receiving a fresh gas input; and outputting a corresponding fresh gas regulation signal by the patient gas measuring unit, wherein the fresh gas input comprises information about a minimal volume flow of the fresh gas to be fed to the breathing gas circuit, which minimal volume flow is to be provided by the fresh gas regulation unit; and receiving the fresh gas regulation signal and selecting the predefined volume flow curve from a number of predefined volume flow curves based on the fresh gas regulation signal.

20. A process in accordance with claim 18, further comprising the steps of:

receiving a limit concentration input; and outputting a corresponding limit concentration signal at the processing unit, wherein the limit concentration input comprises information about a maximum end tidal anesthetic concentration to be provided to a patient to be supplied by the anesthesia device; and outputting of an additional fresh gas correction signal as soon as the defined current end tidal anesthetic concentration in the breathing gas circuit exceeds the maximum end tidal anesthetic concentration to be provided, wherein the originally predefined volume flow curve is correspondingly reduced in response to this additional fresh gas correction signal.

* * * * *